United States Patent
Murray et al.

(10) Patent No.: US 7,935,064 B2
(45) Date of Patent: May 3, 2011

(54) REDUCING OR AVOIDING MUSCLE CRAMPS

(75) Inventors: Robert Murray, Fox River Grove, IL (US); John R. Stofan, IV, Deer Park, IL (US); Jeffrey J. Zachwieja, Cary, IL (US); Craig A. Horswill, Barrington, IL (US); Myron C. Rapkin, Indianapolis, IN (US); Wayne W. Weber, Fortville, IN (US)

(73) Assignee: Stokely-Van Camp, Inc., Chicago, IL (US)

( * ) Notice: Subject to any disclaimer, the term of this patent is extended or adjusted under 35 U.S.C. 154(b) by 0 days.

(21) Appl. No.: 12/183,927

(22) Filed: Jul. 31, 2008

(65) Prior Publication Data
US 2008/0286874 A1    Nov. 20, 2008

Related U.S. Application Data

(62) Division of application No. 11/591,209, filed on Nov. 1, 2006.

(51) Int. Cl.
*A61B 5/05* (2006.01)
*A61B 5/00* (2006.01)
*A61K 47/00* (2006.01)

(52) U.S. Cl. .................. 600/584; 600/346; 424/439

(58) Field of Classification Search .............. 600/346, 600/584; 424/439; 604/20
See application file for complete search history.

(56) References Cited

U.S. PATENT DOCUMENTS

| | | | |
|---|---|---|---|
| 3,552,929 A | 1/1971 | Fields et al. | |
| 3,794,910 A * | 2/1974 | Ninke et al. | 324/442 |
| 4,163,039 A * | 7/1979 | Emrich | 422/56 |
| 4,542,751 A * | 9/1985 | Webster et al. | 600/573 |
| 4,960,467 A * | 10/1990 | Peck | 252/408.1 |
| 5,050,604 A * | 9/1991 | Reshef et al. | 600/346 |
| 5,076,273 A | 12/1991 | Schoendorfer et al. | |
| 5,361,758 A | 11/1994 | Hall et al. | |
| 5,438,984 A * | 8/1995 | Schoendorfer | 600/573 |
| 5,445,606 A * | 8/1995 | Haak et al. | 604/20 |
| 5,465,713 A * | 11/1995 | Schoendorfer | 600/346 |
| 5,638,815 A * | 6/1997 | Schoendorfer | 600/346 |
| 6,051,236 A | 4/2000 | Portman | |
| 6,459,930 B1 * | 10/2002 | Takehara et al. | 600/547 |
| 6,479,015 B1 | 11/2002 | Long et al. | |
| 7,001,612 B2 * | 2/2006 | Armonti et al. | 424/439 |
| 7,314,752 B2 * | 1/2008 | Kritzman et al. | 435/288.7 |
| 7,407,570 B2 | 8/2008 | Prince et al. | |

(Continued)

FOREIGN PATENT DOCUMENTS

EP    0 475 045 A    3/1992

(Continued)

OTHER PUBLICATIONS

International Search Report in related application PCT/US2007/083305, dated Apr. 25, 2008.

(Continued)

*Primary Examiner* — Max Hindenburg
*Assistant Examiner* — Sean P Dougherty
(74) *Attorney, Agent, or Firm* — Banner & Witcoff, Ltd.

(57) ABSTRACT

Muscle cramps can be reduced or avoided by monitoring the concentration of salt in perspiration to indicate the degree of salt depletion. Based on the degree of salt depletion, a sufficient amount of rehydration beverage is consumed to normalize the salt level.

5 Claims, 6 Drawing Sheets

U.S. PATENT DOCUMENTS

| | | | | |
|---|---|---|---|---|
| 2003/0121779 A1* | 7/2003 | Kidwell | .................. | 204/403.01 |
| 2004/0059212 A1 | 3/2004 | Abreu | | |
| 2004/0102931 A1 | 5/2004 | Ellis et al. | | |
| 2004/0217017 A1* | 11/2004 | Kidwell | ........................ | 205/792 |
| 2005/0193554 A1* | 9/2005 | Young et al. | .................... | 29/825 |
| 2006/0052681 A1* | 3/2006 | Aston et al. | .................. | 600/362 |
| 2006/0121548 A1* | 6/2006 | Robbins et al. | ................. | 435/18 |
| 2006/0253011 A1 | 11/2006 | Edmonson et al. | | |
| 2007/0205114 A1* | 9/2007 | Mathur | ........................ | 205/792 |

FOREIGN PATENT DOCUMENTS

| | | |
|---|---|---|
| GB | 1 252 781 A | 11/1971 |
| WO | 2006023985 A | 3/2006 |

OTHER PUBLICATIONS

International Preliminary Report on Patentability issued in related International Patent Application No. PCT/US2007/083305, dated May 5, 2009.

Fluid and Electrolyte Intake and Loss in Elite Soccer Players During Training, Ronald J. Maughan, et al., International Journal of Sport Nutrition and Exercise Metabolism, 2004, 14, pp. 333-346, Copyright 2004 Human Kinetics Publishers, Inc.

Non-Final Office Action issued in related U.S. Appl. No. 12/183,948, dated Oct. 1, 2010.

"Notice of References Cited" listed in Notice of Allowance issued for related U.S. Appl. No. 11/591,209, dated Sep. 30, 2010, p. 8.

Office Action in related U.S. Appl. No. 12/183,948 mailed Jan. 21, 2011.

* cited by examiner

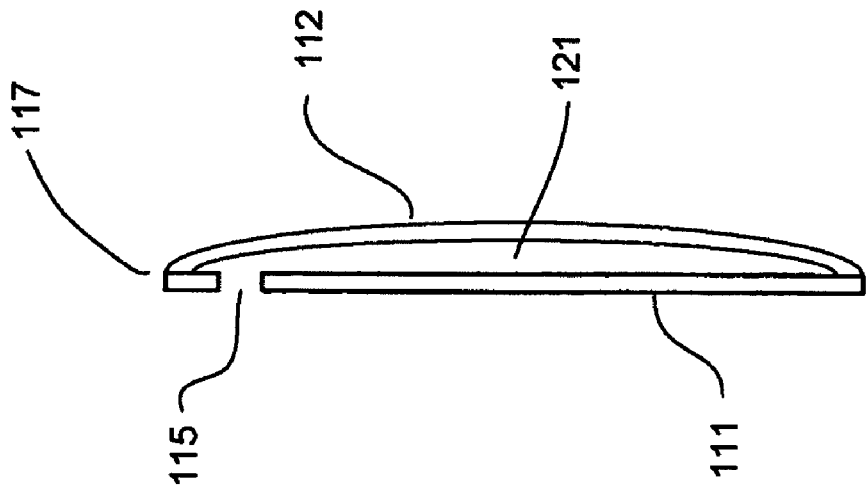
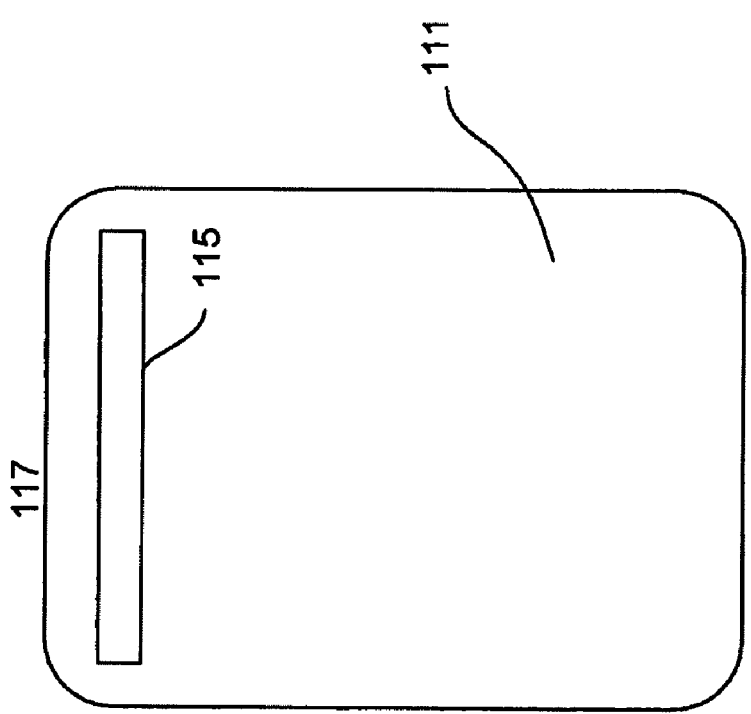

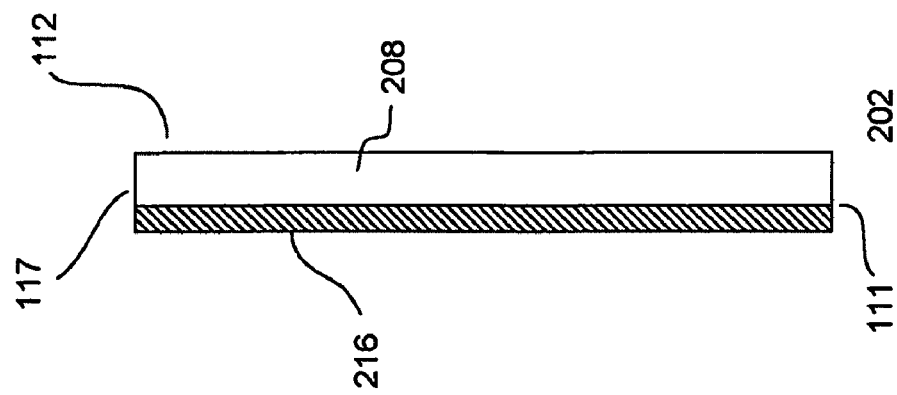
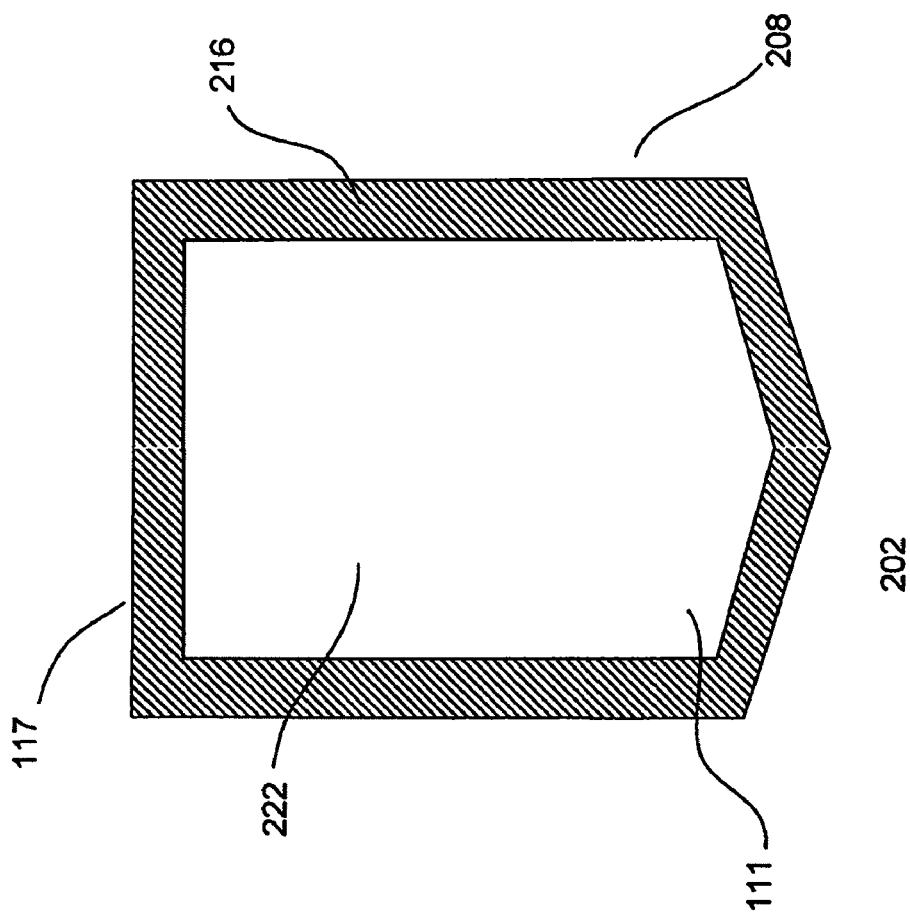

REDUCING OR AVOIDING MUSCLE CRAMPS

CROSS-REFERENCE TO RELATED APPLICATIONS

This application is a divisional of U.S. patent application Ser. No. 11/591,209, entitled "Reducing or Avoiding Muscle Cramps," filed Nov. 1, 2006, which is incorporated in its entirety, herein by reference.

FIELD OF THE INVENTION

The present invention relates generally to avoiding muscle cramps and more particularly to monitoring salt depletion to indicate likelihood of cramping.

BACKGROUND OF THE INVENTION

Muscle cramps, the involuntary and forceful contraction of muscles, are painful and can last for a prolonged period of time. During physical activities in hot weather conditions, cramps appear to occur more often. Such types of cramps are commonly referred to as heat cramps. Due to the pain and lack of movement of the affected limb, the physical activity is interrupted at least until the cramping stops. Even then, re-exerting the muscle may cause the cramping to reoccur. As such, muscle cramping can impact an athlete for a prolonged period of time. In the case of an athletic competition, its outcome can be adversely impacted due to withdrawal of or inability to perform by the affected athlete.

From the foregoing discussion, it is desirable to reduce or avoid muscle cramps from occurring.

SUMMARY OF THE INVENTION

The present invention relates to reducing or avoiding muscle cramps. Muscle cramps can be reduced by monitoring salt or ionic loss to estimate adequate replacement of such salt during, for example, physical activity. To monitor ionic loss, a perspiration sample is collected and tested. The invention can also be used to test ionic content of other types of body fluids collected or using the results for other purposes. In addition, cramps can be easily and conveniently reduced or avoided, decreasing the likelihood of disruptions in physical activities, such as exercising or athletic competitions.

In one aspect, a method is disclosed which monitors the possibility of muscle cramps by collecting a test sample of body fluid and analyzing the sample to provide a result which indicates a degree of ionic depletion. Based on the degree of ionic depletion, dosage information can be provided to replenish the body with sufficient amounts of such things as salt to reduce the likelihood of cramping.

In another aspect, a kit is disclosed for reducing muscle cramps. The kit comprises a sample collection unit having a pouch with first and second surfaces and a space therebetween. An opening is located at or near a first end of the pouch. The opening facilitates collection of a sample of body fluid when the collection unit is dermally mounted onto the skin of a test subject. The kit also includes a tester which includes a test portion. The test portion, when exposed to the sample after it has been collected, reacts with the sample to produce a result indicating the degree of ionic depletion from the test subject.

In yet another aspect, the invention is directed to a product for reducing muscle cramps. The product comprises a primary product which contains salt. A kit is provided with the primary product. The kit includes a sample collection unit having a pouch with first and second surfaces and an opening located at or near a first end thereof. The opening facilitates collection of a sample of body fluid when the collection unit is dermally mounted onto the skin of a test subject. A tester is provided with the kit. The tester includes a test portion which, when exposed to the sample after it has been collected, reacts with the sample to produce a result indicating the degree of ionic depletion from the test subject.

These and other objects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIGS. 1a-b show different views of a sample collection unit in accordance with one embodiment of the invention;

FIGS. 2a-b show different views of a sample collection unit in accordance with another embodiment of the invention;

DETAILED DESCRIPTION OF THE INVENTION

Figure 4:
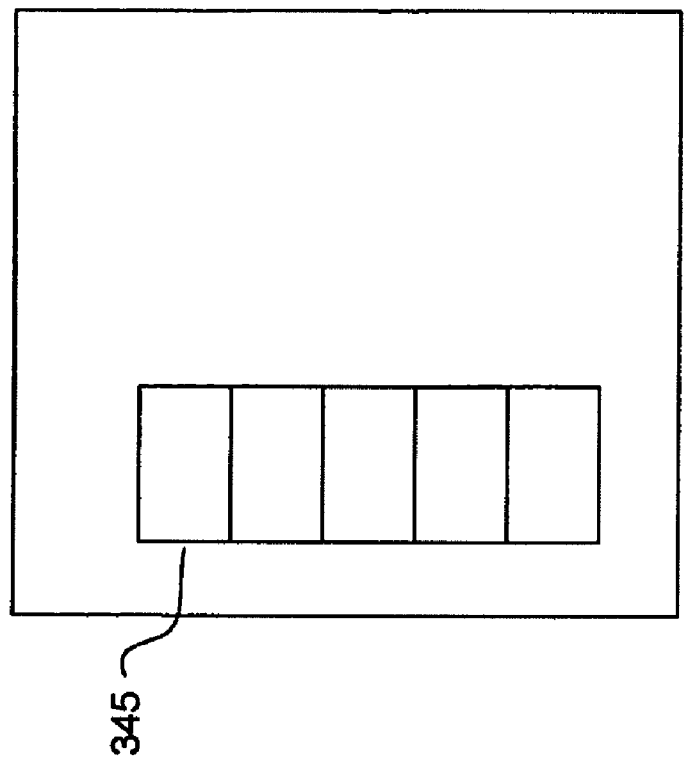
FIG. 4 shows a test chart in accordance with one embodiment of the invention.

The present invention relates to reducing or avoiding muscle cramps. Muscle cramps can be reduced by monitoring ionic or salt loss during, for example, physical activity. To monitor salt loss, a perspiration sample is collected and tested. Testing salt content from other types of body fluids collected or using the results for other purposes, such as urine, is also contemplated within the scope of the invention.

FIGS. 1a-b show plan and side views of a collection unit 101 used to collect a sample for testing in accordance with one embodiment of the invention. The collection unit collects and stores perspiration ("sample") from the body for testing. As shown, the collection unit comprises a pouch having a space 121 between first and second sides 111 and 112. The pouch can have various shapes. The pouch can be, for example, rectangular in shape with rounded corners, as shown. Providing a pouch with other geometric shapes is also useful. In one embodiment, an opening 115 is provided at or near a first end 117 of the pouch to facilitate collection and storage of the sample in the space. The size of the pouch should be sufficient to hold at least a desired amount of the sample for testing. Typically, the amount of sample to be tested is about 10-30 ml, but can optimally be ½ oz. or 15 ml. and can range from as low as 5 ml. with no specific upper range. The dimensions of the pouch are, for example, about 6 cm. by about 9½ cm. Other dimensions may also be useful, and any size pouch can be used that can comfortably be attached to the body.

In one embodiment, the pouch is formed by attaching or bonding the edges of first and second layers together leaving the interior portion un-bonded to create the space. Other techniques for forming the pouch can also be useful. Such techniques, for example, can include injection or blow molding; however, there are any number of other methods of creating the pouch. The pouch should be formed from a material which can adequately store or hold the collected sample. In one embodiment, material for forming the pouch comprises 3M's Tegaderm® trademarked product or Pharm Check's Pharmcheck® trademarked product, both of which are available on the market. Other materials are any type of material that can be flexible and waterproof.

The opening can be provided by not bonding the edges of the layers at the first end 117 of the pouch. Alternatively, the opening is provided near the first end of the first layer. The opening should be sufficiently large to enable collection of the sample. In one embodiment, the opening extends to at least half the width of the pouch. Preferably, the opening extends to at least ¾ the width of the pouch. More preferably, the opening extends to about 90 percent of the width of the pouch.

To facilitate the flow of the sample into the pouch, an absorbent layer (not shown) can be provided at the opening. Various types of materials which enhance the collection of the sample can be used to form the absorbent layer. Such materials can include, for example, fibrous materials and/or hydrophilic membranes. For example, the absorbent layer can be formed from hydrophilic polymer fibers such as polycarbonate, cellulose acetate, nylon or a combination thereof. Other types of materials, such as natural fibers which include paper, cloth cellulose or synthetic fibers can also be used. However, it must be verified that such material does not affect the salt content of the collected liquid.

The absorbent layer, in one embodiment, includes a first portion that extends outside of the opening and a second portion disposed inside the space. Other configurations of the absorbent layer are also useful. An adhesive may be used to fix the absorbent layer to the pouch. The adhesive may also be provided to fix the portion of the absorbent layer which extends out of the opening to the skin. Various types of adhesives can be used, including any adhesive that is used in medical or personal care products. Preferably, the adhesive used should not interact with the sample, causing contamination and which may produce inaccurate test results. Preferred adhesives include any type of adhesive used in medical or cosmetic uses.

In one embodiment, an adhesive is disposed on the outer surface of the first layer of the pouch. The adhesive temporarily attaches the collection unit to the skin of the user. The use of an adhesive allows the collection unit to be conveniently attached to various parts of the body. For example, the collection unit can be attached to a part of the body which facilitates collection of the sample as well as being easily accessed by the user. Typically, the collection unit is attached to the chest or waist. Attaching the collection unit to other parts of the body is also useful. Various types of adhesives can be used. Preferably, an adhesive which is inert with the sample is used. Additionally, the adhesive used should not cause skin irritation to the user. Other types of adhesives, such as those used in topical patches or adhesive tapes are also useful. Alternatively, the collection unit can be mounted to the skin using a strap or belt which fixes it to the body. For example, the collection unit can be fixed in this manner to the chest, waist or other parts of the body. When attached to the body, the collection unit is preferably oriented so that the opening is located at the top or substantially at the top. As the user perspires, gravity causes the sweat to flow downwards through the opening and into the pouch. The absorbent layer further attracts the sweat through the opening and into the pouch.

FIGS. 2*a-b* show plan and side views of a collection unit 202 in accordance with another embodiment of the invention. As shown, the collection unit comprises a patch having a layer 208 with first and second sides 111 and 112. The pouch can have various shapes. The pouch, for example, can have a pentagonal shape, with three sides being arranged in 90.degree. angles to each other while the other two sides being a V, forming a shape similar to that of a pocket. Providing a pouch with other geometric shapes is also useful. The layer should be formed from a material which can adequately store or hold the collected sample. For example, the layer can be formed from the products described above.

An adhesive 216 is disposed on a first surface of the patch. In one embodiment, the adhesive is disposed at about the circumference of the patch, leaving the internal portion 222 of the patch devoid of the adhesive. The adhesive temporarily attaches the collection unit onto the skin of the user. The use of an adhesive allows the collection unit to be conveniently attached to various parts of the body. Preferably, the patch is oriented such that the V is located toward the bottom of the patch, closer to the ground. The patch can also be attached to the skin with other orientations.

When attached, the patch forms a cavity or space between it and the skin, sealed by the adhesive. The cavity corresponds to the inner portion of the patch which does not contain adhesive. Sweat collected is then stored in this cavity until ready for testing. Testing can be conducted by lifting a top edge 17 of the patch is lifted off the skin to form an opening though which a tester can be dipped to access the sample. In an alternative embodiment, the opening can be provided by not providing adhesive at least at a portion of the top edge 117. The portion should be sufficiently large to create an opening though which a tester can pass.

A tester or test strip can be used by inserting it into the pouch after the sweat has been collected. The tester can be made to turn colors depending on the content of the sweat. The tester can then be removed from the pouch and compared, for example, to a color strip which informs the user of the ionic or salt concentration in the sweat; each color identifies a different concentration level. In the alternative, a test strip can be located in the pouch, and the color strip can be either outside—so the comparison can be made by comparing the test strip color through a see-through pouch—or both the test strip and the color strip can be within the pouch with both visible through the see-through pouch.

Figure 3:
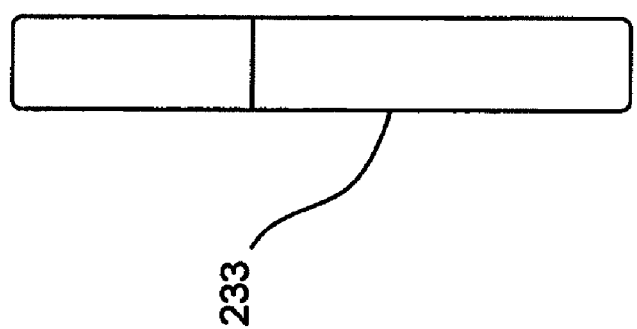
FIG. 3 shows a tester in accordance with one embodiment of the invention.

FIG. 3 shows a tester 204 in accordance with one embodiment of the invention. The tester, for example, comprises a test strip which includes a test portion 233. Typically, the tester is made from a material, such as filter paper, which is able to absorb the sample. To test the sample, the tester is dipped into the pouch via the opening such that the test portion comes into contact with the sample. The test portion of the tester produces a result based on the content of a target component in the sample. The tester, in one embodiment, produces a result based on the salt content of the perspiration sample, indicating the degree of salt depletion. Testing for other types of target components is also useful.

In one embodiment, the tester utilizes a colorimetric technique to determine the content of a target component in the sample, such as the ionic load of the sweat. Typically, a reagent which reacts with salt is disposed in the test portion. In one embodiment, the reagent reacts with chloride. Other elements that can be measured include sodium, the specific gravity, pH, proteins, urea, ketones, lactate, magnesium or potassium. The reaction causes the test portion to develop a specific color depending on the concentration of the target component. The result from the tester indicates the degree of ionic depletion.

In another embodiment, the test portion can include a plurality of segments with respective reagents or reagent compositions. A segment which corresponds to the salt concentration in the sample reacts and develops accordingly, for example, a specified color. Other types of measurement can include measuring an electrical current through the sweat as a measurement of the ionic load of the sweat.

FIG. 4 shows a test chart 305 in accordance with one embodiment of the invention. The test chart includes information regarding the test results. In one embodiment, the test chart includes information which indicates the degree of salt depletion based on the information provided by the tester. In one embodiment, a color scale 345 is provided in the test chart. Other types of scales can be useful, depending on the application. Various colors corresponding to the colors that can be generated by the tester are included in the color scale. The scale can be arranged with discrete colors or a continuous color spectrum which includes color transitions or gradients from one color to the other. The continuous color spectrum can be parsed into segments corresponding to a degree of salt depletion.

Figure 7:
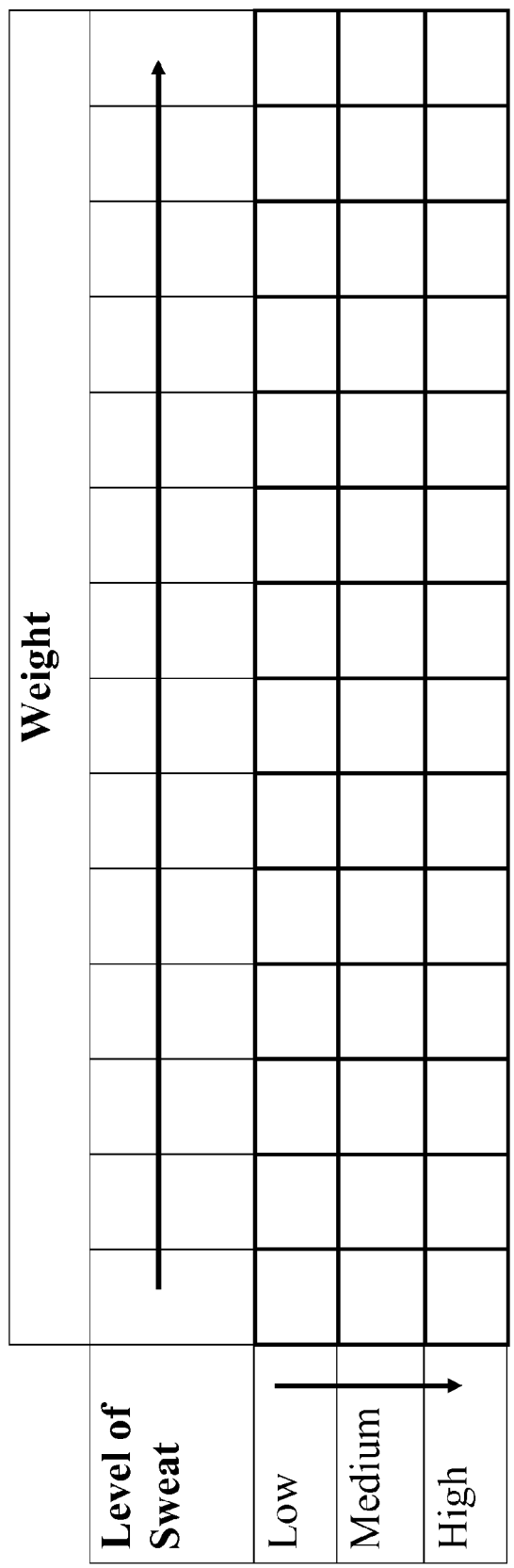
FIG. 7 shows a table in accordance with one embodiment of the invention.

The ionic load of the sweat if one factor in determining if ionic replacement is required. The other factor is the quantity of sweat secreted from the body. Thus, ideally, a total ionic depletion can be measured through measuring the loss of weight of the person through sweat as well as the level of ionic concentration in the sweat. With that total depletion, the quantity of ionic replacement required can be calculated. However, the calculation need not be so exact. For example, the user may estimate total sweat loss by determining whether the level of sweat has been low, medium or high and by knowing the user's weight. So, for example, tables, such as shown in FIG. 7, may be provided that estimate total sweat based on the level of sweat (low, medium or high) and the person's weight. This information can then be combined with the ionic concentration in the sweat to determine the ionic replacement required.

The test chart can also include dosage information, for example, about an amount of salt and liquid to consume based on the degree of salt depletion. The dosage information can be general or related to one or more specific products available in the market for oral rehydration purposes, for example, sports or energy beverages such as Propel® or Gatorade® from PepsiCo.

Figure 5:
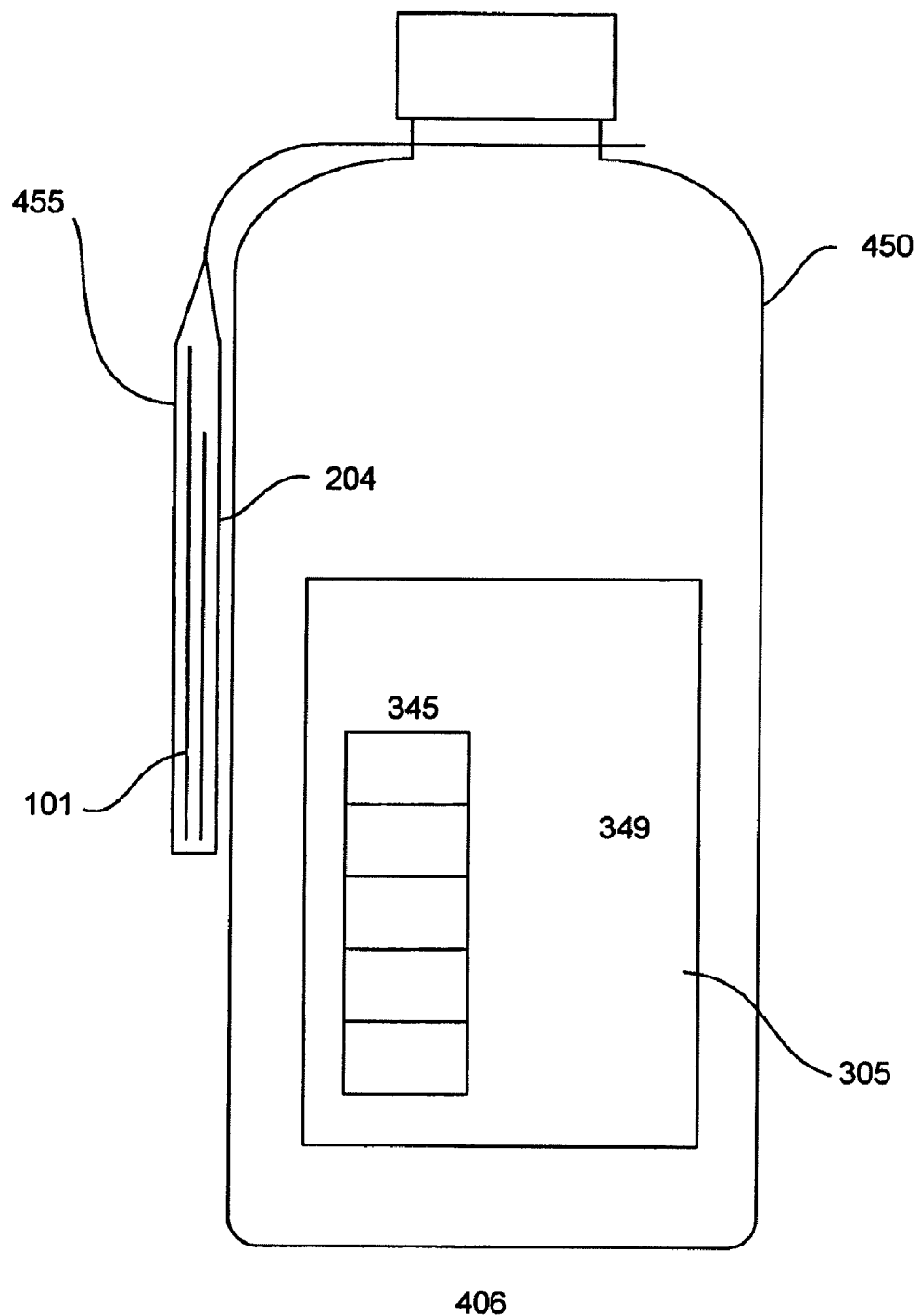
FIG. 5 shows a product package including a test kit in accordance with one embodiment of the invention.

In accordance with one embodiment of the invention, the collection unit, tester and test chart form a kit to enable users to monitor the degree of salt loss. FIG. 5 shows a product package 406 in accordance with one embodiment of the invention. The product package comprises a primary product 450 and a kit for monitoring salt loss. The primary product (PP), in one embodiment, comprises a salt containing oral rehydration beverage. The beverage can be any type of sports or energy beverage. For example, the beverage can comprise Gatorade® or Propel® marketed by PepsiCo. As shown, the PP is packaged in a bottle-type container. The beverage can also be packaged in other types of containers. Providing a beverage in powder or gel form to be mixed with a liquid for consumption is also useful. Packaging the kit with any type of products is also useful.

The kit, which is provided with the PP, includes a collection unit 101, a tester 204 and a test chart 305 as described above. A portion 349 of the test chart may comprise dosage information. In one embodiment, the dosage information includes at least the amount of PP to be consumed based on the test result may be provided in portion 349 of the test chart. Dosage information of other types of products or general dosage information can also be provided. Additionally, the PP package may include markings corresponding to dosage amounts indicated in the test chart. This is particularly useful for transparent type of PP packages or where dosage amounts can be less than the total amount of PP contained in the PP package.

A kit package 455 is provided to contain at least some of the kit components. In one embodiment, the kit package includes the collection unit and tester while the test chart is provided with or attached onto the PP package. Other kit packaging arrangements, such as including all components of the kit in the kit package, are also useful. The kit package is attached to the PP package. Various techniques can be used for attaching the kit package to the PP package. For example, a bottle net hanger can be provided to attach the test kit to the neck of the PP package. Alternatively, the kit package can be attached to the PP package using an adhesive.

As described, the product package includes one PP and one kit comprising of one each of collection unit, tester and test chart. Other product package arrangements are also useful. For example, it is not necessary that there is a one to one correspondence with each component of the product package. In some applications, it may be desirable to provide numerous kits per PP or numerous testers within a kit. The packaging arrangement can be tailored for specific applications or needs. Furthermore, the kit or components of the kit can be marketed individually.

Figure 6:
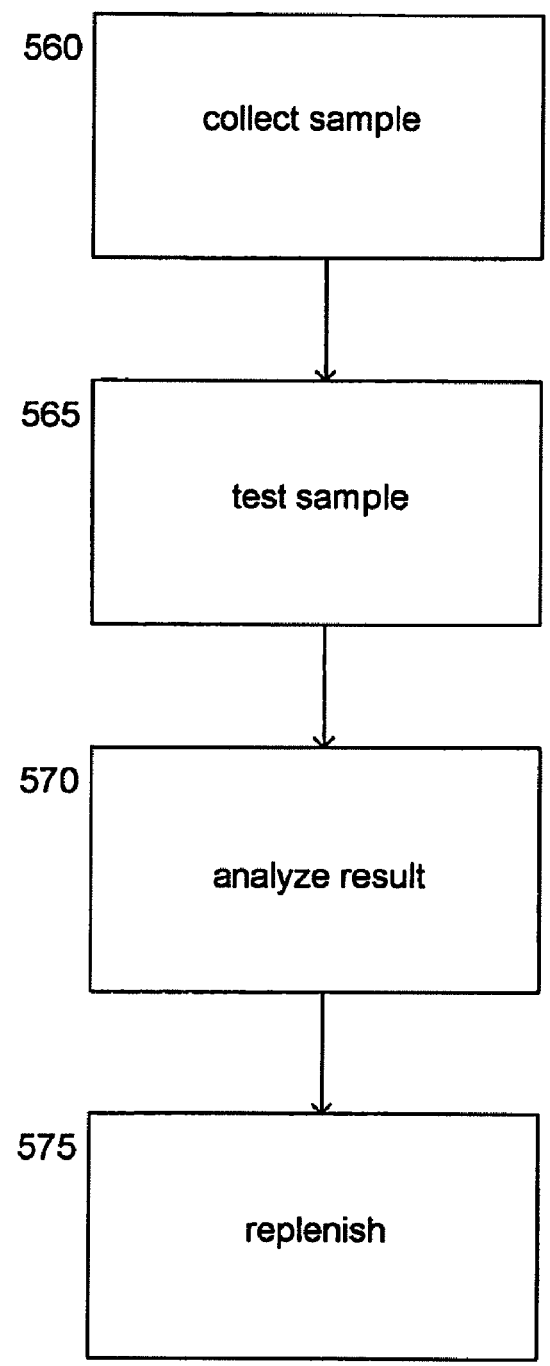
FIG. 6 shows a process for reducing or avoiding muscle cramps in accordance with one embodiment of the invention.

FIG. 6 shows a method, in accordance with one embodiment of the invention, for reducing or avoiding cramps, for example, during physical activities. Over the course of physical activity, sweating occurs. At step 560, a perspiration sample is collected from the user. In one embodiment, the perspiration sample is collected using a collection unit which is attached to the body. Other techniques for collecting perspiration samples may also be useful. The collected sample is tested to determine its salt content at step 565 to indicate the degree of salt depletion. Testing is conducted using a tester. The tester, for example, employs a colorimetric technique. Other test techniques are also useful.

The test results, at step 570, are analyzed. The analysis involves, for example, using a test chart which contains a scale for determining the degree of salt loss based on the test result. In one embodiment, the test chart comprises a color chart which indicates the degree of salt depletion based on the color of the tester after testing. Based on the degree of salt loss, the appropriate dosage of salt and liquid to consume can be determined. In one embodiment, the dosage information can be provided in the test chart. This conveniently enables the user to determine the amount of salt needed. The dosage information can be directed to a specific product, such as a rehydration beverage (e.g., Gatorade®). At step 575, the user consumes the recommended amount of rehydration beverage to sufficiently replenish the body with normal level of salt. By monitoring the degree of salt depletion, muscle cramps can be reduced or avoided, particularly with individuals who are early, heavy and salty sweaters.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A method of limiting muscle cramping comprising:
providing a packaging having a consumable composition comprising at least one salt and a table providing an estimate of a quantity of sweat secreted during physical activity based on a level of sweat and a weight of a user;
providing with the packaging, a tester including a test portion configured to be exposed to body fluid of the user for use in obtaining a result indicative of an estimated degree of predicted muscle cramping from the user;
providing a test chart associated with the packaging configured to be compared with the tester after exposure to the body fluid to provide a test result of an estimated degree of muscle cramping; and
providing dosage information regarding the consumable composition, the dosage information comprising an amount of the consumable composition to be consumed by the user based on the test result for salt replenishment and the estimate of a quantity of sweat secreted during physical activity, sufficient to substantially limit muscle cramping.

2. The method of claim 1, wherein the tester is configured to measure a concentration of components selected from the group consisting of: proteins, urea, ketones, lactate, magnesium, potassium and combinations thereof.

3. The method of claim 1, wherein the body fluid comprises perspiration.

4. The method of claim 1, wherein the consumable composition comprises a beverage.

5. The method of claim 1, wherein the consumable composition comprises a rehydration beverage concentrate and the dosage information comprises information in preparing a rehydration beverage from the rehydration beverage concentrate.

* * * * *